(12) United States Patent
Isola et al.

(10) Patent No.: US 10,441,811 B2
(45) Date of Patent: Oct. 15, 2019

(54) RADIOTHERAPY PLANNING SYSTEM AND METHOD

(71) Applicant: KONINKLIJKE PHILIPS N.V., Eindhoven (NL)

(72) Inventors: Alfonso Agatino Isola, Eindhoven (NL); Christoph Neukirchen, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 464 days.

(21) Appl. No.: 15/314,698

(22) PCT Filed: Jun. 25, 2015

(86) PCT No.: PCT/EP2015/064328
§ 371 (c)(1),
(2) Date: Nov. 29, 2016

(87) PCT Pub. No.: WO2016/001046
PCT Pub. Date: Jan. 7, 2016

(65) Prior Publication Data
US 2017/0189715 A1 Jul. 6, 2017

(30) Foreign Application Priority Data
Jun. 30, 2014 (EP) .................................. 14174905

(51) Int. Cl.
*A61N 5/10* (2006.01)
*G06F 19/00* (2018.01)
*G06N 3/12* (2006.01)

(52) U.S. Cl.
CPC ......... *A61N 5/1031* (2013.01); *A61N 5/1048* (2013.01); *G06F 19/325* (2013.01);
(Continued)

(58) Field of Classification Search
CPC .................. A61N 5/103; A61N 5/1031; A61N 2005/1032
See application file for complete search history.

(56) References Cited

U.S. PATENT DOCUMENTS 7,831,289 B2    11/2010  Riker et al.
9,507,886 B2 *  11/2016  Fiege ................... A61N 5/1031
(Continued)

OTHER PUBLICATIONS

Salari, et al., "Exploring Trade-offs between VMAT Dose Quality and Delivery Efficiency using a Network Optimization Approach", Phys Med Biol. Sep. 7, 2012; 57(17): 5587-5600.
(Continued)

*Primary Examiner* — Thomas R Artman

(57) ABSTRACT

The present invention relates to a radiotherapy planning system (100) for determining a solution (101) corresponding to a fluence profile. The invention proposes to use a Pareto frontier navigator (140) to select the best plan from a set of various auto-planned solutions. An interactive graphical user interface (400) is provided to the planner to navigate among convex combinations of auto-planned solutions. This proposed Pareto plan navigation can be considered as a further optional refinement process, which can be applied to find the best plan in those cases where auto-generated solutions are not fully satisfying the planner's requirements. The navigation tool (400) moves locally through a set of auto-generated plans and can potentially simplify the planner's decision making process and reduce the whole planning time on complex clinical cases from several hours to minutes.

13 Claims, 5 Drawing Sheets

(52) U.S. Cl.
CPC ........... *G06F 19/3481* (2013.01); *G06N 3/12* (2013.01); *A61N 5/103* (2013.01); *A61N 2005/1032* (2013.01); *A61N 2005/1074* (2013.01); *G06F 19/34* (2013.01)

(56) References Cited

U.S. PATENT DOCUMENTS

| | | | |
|---|---|---|---|
| 2005/0038762 A1* | 2/2005 | Grefenstette | G06N 3/126 706/13 |
| 2005/0116172 A1 | 6/2005 | Trinkaus et al. | |
| 2009/0037150 A1 | 2/2009 | Craft et al. | |
| 2011/0085643 A1 | 4/2011 | Zhu et al. | |
| 2013/0197878 A1 | 8/2013 | Fiege et al. | |
| 2013/0326405 A1 | 12/2013 | Nord et al. | |
| 2015/0141733 A1 | 5/2015 | Kumar et al. | |
| 2017/0189715 A1* | 7/2017 | Isola | A61N 5/1031 |

OTHER PUBLICATIONS

Wala, et al., "Maximizing dosimetric benefits of IMRT in the treatment of localized prostate cancer through multicriteria optimization planning", Medical Dosimetry 38 (2014) 298-303.

Hong, et al., "Multicriteria optimization in intensity-modulated radiation therapy treatment planning for locally advanced cancer of the pancreatic head", Int J Radiat Oncol Biol Phys. Nov. 15, 2008; 72(4): 1208-1214.

Kashani, R., et al., "MO-D-BRB-07:Automated IMRT Plan Generation for Prostate Cancer", Med. Phys. (2010), vol. 37, pp. 3340.

Zarepisheh, M. et al., "A DVH-guided IMRT optimization algorithm for automatic treatment planning and adaptive radiotherapy replanning". Medical Physics, vol. 41, No. 6, p. 061711 (2014).

Craft, D. et al.; "Deliverable navigation for multicriteria step and shoot IMRT treatment planning", Phys. Med. Biol. (2013), vol. 58, pp. 87-103.

Craft, D. et al., "Approximating convex Pareo surfaces in multiobjective radiotherapy planning", Med. Phys. (2006), 33(9) pp. 3399-3407.

Craft, D. et al., "Simultaneous navigation of multiple Pareto surfaces, with an application to multicriteria IMRT planning with multiple beam angle configurations", Med. Phys. (2010), 37(2) pp. 736-741.

Monz, M. et al., "Pareto navigation—algorithmic foundation of interactive multi-criteria IMRT planning", Phys. Med. Biol. (2008), vol. 53, Abstract.

De Berg, M. et al., "Computational Geometry: Algorithms and Application", Springer, pp. 2-8, 2000.

Knuth, D.E. "Axioms and hulls", lecture Notes in Computer Science No. 606, Heidelberg: Springer-Verlag, p. ix + 109, 1992.

Boyd, S. et al., "Convex Optimization", Cambridge University press, ISBN 978-0-521-83378-3, (2004).

Kuper, K.H. et al., Multicriteria optimization in intensity modulated radiotherapy planning. (2005).

Janssen, T., et al., "Pareto fronts in clinical practice for pinnacle", Int J Radiat Oncol Biol Phys, Mar. 1, 2013;85(3); Abstract.

Li, N. et al., "Automatic treatment plan re-optimization for adaptive radiotherapy guided with the initial plan DVHs", Physics in Medicine and Biology, vol. 58, No. 24, 2013, Abstract.

* cited by examiner

RADIOTHERAPY PLANNING SYSTEM AND METHOD

CROSS-REFERENCE TO PRIOR APPLICATIONS

This application is the U.S. National Phase application under 35 U.S.C. § 371 of International Application Serial No. PCT/EP2015/064328, filed on Jun. 25, 2015, which claims the benefit of European Patent Application No. 14174905.1, filed on Jun. 30, 2014. These applications are hereby incorporated by reference herein.

FIELD OF THE INVENTION

The present invention relates to a radiotherapy planning system, a radiotherapy planning method, and a computer readable storage medium for determining a radiotherapy planning solution corresponding to a fluence profile.

BACKGROUND OF THE INVENTION

The main goal of radiotherapy planning (RTP) is to determine fast and accurately the best dose distribution (i.e., fluence beam profile) which can satisfy as much as possible all clinical goals. For instance, a certain dose must be delivered to the tumor, sparing as much as possible nearby organs at risk (OARs). Therefore, optimization problems in radiotherapy (RT) inverse planning are inherently multi-criteria problems since they involve multiple planning goals for tumor targets and neighboring critical tissue structures. Clinical decisions are generally required, commonly based on an assignment of importance weights among these conflicting goals until the clinical wishes appear satisfied. Satisfying the clinical wishes typically involves many repetitive optimizations. Recently, in treatment planning systems (TPS) such as, e.g., the Philips Pinnacle$^3$ treatment planning system, "auto-planning" routines have been included to automatically generate plans which can satisfy clinical requirements, see the article "*MO-D-BRB-07: Automated IMRT Plan Generation for Prostate Cancer*", Med. Phys. (2010), Vol. 37, pp. 3340-3340 by R. Kashani et al., which is incorporated herein by reference. The implementation of these auto-planning routines relies on 'scripts,' which are assemblies of internal commands stored as text files. Scripts can be called at any time on new patient files.

US2013197878A1 discloses a fluence and beam orientation optimization package for radiotherapy optimization, called PARETO (Pareto-Aware Radiotherapy Evolutionary Treatment Optimization), making use of a multi-objective genetic algorithm capable of optimizing several objective functions simultaneously and mapping the structure of their trade-off surface efficiently and in detail. PARETO generates a database of Pareto non-dominated solutions and allows the graphical exploration of trade-offs between multiple planning objectives during IMRT treatment planning PARETO offers automated multi-objective treatment plan optimization, which does not require any objective weights to be chosen, and therefore finds a large sample of optimized solutions defining a trade-off surface, which represents the range of compromises that are possible.

When invoked on a new patient, an auto-planning routine typically creates various target and normal tissue planning structures, sets up the beams and dose prescription, and loads customized intensity modulated radiation therapy (IMRT) objectives to start the optimization. Target objectives are based on the prescription dose, while organ at risk objectives are determined from a model that takes into account the geometric properties of the target and organs at risk to predict mean doses based on prior cases. Unfortunately, the time needed and quality achieved with auto-planning optimization is case dependent. Only rarely, the first auto-planned solution is clinically approved without further interaction. Rather, more frequently, additional manual parameter tweaking is required to meet as many clinical goals as possible. This additional refinement step of tweaking the parameters manually can take up to several hours, thereby diluting the benefits of auto-planning in the radiotherapy planning workflow.

The article "*A DVH-guided IMRT optimization algorithm for automatic treatment planning and adaptive radiotherapy replanning*" by M. Zarepisheh et al, Medical Physics, vol. 41, no. 6, page 061711 (2014) discloses an algorithm that automatically creates a treatment plan guided by the DVH curves of a reference plan that contains information on the clinician-approved dose-volume trade-offs among different targets/organs and among different portions of a DVH curve for an organ. In ART, the reference plan is the initial plan for the same patient, while for automatic treatment planning the reference plan is selected from a library of clinically approved and delivered plans of previously treated patients with similar medical conditions and geometry. The proposed algorithm employs a voxel-based optimization model and navigates the large voxel-based Pareto surface. The voxel weights are iteratively adjusted to approach a plan that is similar to the reference plan in terms of the DVHs. If the reference plan is feasible but not Pareto optimal, the algorithm generates a Pareto optimal plan with the DVHs better than the reference ones. If the reference plan is too restricting for the new geometry, the algorithm generates a Pareto plan with DVHs close to the reference ones. In both cases, the new plans have similar DVH trade-offs as the reference plans.

SUMMARY OF THE INVENTION

It is an object of the present invention to provide an improved radiotherapy planning system and method for determining in a fast and accurate manner a solution corresponding to a fluence profile.

According to a first aspect of the present invention, there is provided a radiotherapy planning system for determining a solution corresponding to a fluence profile, the radiotherapy planning system comprising: an auto-planned solution generation unit for automatically generating one or more auto-planned treatment plans based on one or more dose quality metrics; a weight assignment unit configured to assign a predetermined plurality of weights to said one or more dose quality metrics; a weight adjustment unit configured to adjust a selected weight from said plurality of weights; and a Pareto frontier navigation unit configured to generate said solution corresponding to said fluence profile in response to said adjusted selected weight. The radiotherapy planning system is configured to compare said solution to a clinical goal and wherein said radiotherapy planning system is further configured to generate a comparison signal indicative of whether or not said solution satisfies said clinical goal.

Herein, it is proposed to use a Pareto frontier navigator as described, e.g., in the article "*Deliverable navigation for multicriteria step and shoot IMRT treatment planning*", Phys. Med. Biol. (2013), Vol. 58, pp. 87-103 by D. Craft and C. Richter, which is incorporated herein by reference, to select the best plan from a set of various auto-planned solutions.

In multi-criteria optimization theory, several approaches have been proposed to find the best tradeoff between several (conflicting) objectives. Most common is the so-called "weighted method" (or "scalarization" approach), where a composite functional consisting of the weighted sum of all objectives is minimized. Here, a decision maker is asked to find the best set of weights which can lead to the preferred solution. This approach is commonly used in traditional IMRT fluence map optimizations. Another method for multi-criteria optimization is the "Goal programming" method. Here, the decision maker already knows the desired value for each objective. Then, a least-squared-problem is minimized to find the best solution, which minimizes the distance from this reference vector of desired values. Other approaches are also available like "lexicographic ordering" optimization, etc.

Another family of multi-criteria optimization approaches comprises the so-called "interactive methods". In interactive methods, a decision maker plays an important part and the idea is to support her/him in the search for the most preferred solution. In interactive methods, steps of an iterative solution algorithm are repeated and the decision maker progressively provides preference information so that the most preferred solution can be found. The Pareto frontier navigator of the present invention is part of this last group of methods. Pareto navigators are known to the skilled person and described, e.g., in the article "*Approximating convex Pareto surfaces in multiobjective radiotherapy planning*", Med. Phys. (2006), 33(9) pp. 3399-3407, by D. L. Craft et al., and in the article "*Simultaneous navigation of multiple Pareto surfaces, with an application to multicriteria IMRT planning with multiple beam angle configurations*", Med. Phys. (2010), 37(2) pp. 736-741, by D. Craft et al.

Hereto, a simple and interactive graphical user interface (GUI) is provided to the planner to "navigate" among convex combinations of auto-planned solutions. This proposed Pareto plan navigation can be considered as a further optional refinement process, which can be applied to find the best plan in cases where auto-generated solutions are not fully satisfying planner's requirements. Such a navigation tool that moves locally through a set of auto-generated plans can potentially simplify the planner's decision making process and reduce the whole planning time on complex clinical cases from several hours to minutes. The expression "move locally" indicates varying the potential solution obtained in step 0 below only within a limited range (i.e., locally).

Preferably, at step 0 below, a first 'auto-generated' solution is produced, e.g., by using the Pinnacle 3 Auto-planning tool. Then, the planner may either accept and deliver this solution (i.e., beam fluence profiles) or refine it.

If a refinement is needed, then the present invention can be used to make the refinement step easier and faster.

Indeed, at step 1, a Pareto front is preferably approximated by optimizing N+1 plans as described below. Since it is desired to "refine" the first solution produced at step 0, the Pareto matrix Y will be populated with (N+1)+1=N+2 plans (i.e., N "anchor" plans, plus the "balance" plan, plus the initial auto-generated plan at step (0)).

When the navigation starts, the initial position from where one starts to move within the Pareto solution space corresponds to the solution obtained at step 0. The user can move the sliders to further move towards a new local Pareto solution which may better fit his requirements.

Preferably, said radiotherapy planning system further comprises an auto-generated solution assessment unit for deciding whether at least one of said one or more auto-planned treatment plans satisfies a clinical goal. Preferably, said radiotherapy planning system is configured to use a Pareto frontier navigator. By using a Pareto frontier navigator, the radiotherapy planning system finds the best final plan within a local neighborhood of a limited set of auto-planned solutions. Preferably, after determining a Pareto matrix, a tool is provided that allows the planner to navigate within the Pareto optimal space. By providing a tool that allows the planner to navigate within the Pareto optimal space, the radiotherapy planning system finds the best tradeoff between all target and OAR's dose objectives. Preferably, if said comparison signal indicates that said solution does not satisfy said clinical goal, said radiotherapy planning system is further configured to provide said solution as a warm start to generate a final auto-generated plan.

According to a preferred embodiment, said Pareto frontier navigation unit is configured to determine a convex hull piecewise linear approximation of a Pareto front. In particular, it is preferred that the proposed navigator will move within a convex hull piecewise linear approximation $Y^c$ of the Pareto front, as described in the article "*Pareto navigation—algorithmic foundation of interactive multi-criteria IMRT planning*", Phys. Med. Biol. (2008), Vol. 53, pp. 985-998, by M. Monz et al., which is incorporated herein by reference:

$$Y^c = \left\{ \sum_{k=1}^{N+2} v_k f(x_k) \middle| \sum_{k=1}^{N+2} v_k = 1, v \geq 0 \right\}.$$

Here v is the vector of convex combination weights for each navigated solution in $Y^c$, $x_k$ refers to an auto-generated plan, with k=1, ..., N+2, and $f$ is a vector-valued function, where each component is one of N dose quality metrics.

According to a further preferred embodiment, said weight adjustment unit comprises a graphical user interface, where, for each respective weight from said plurality of weights, a slider is provided to adjust said respective weight. By providing a graphical user interface with adjustment sliders for each respective weight from said plurality of weights, the user is offered a simple and interactive tool to tune the parameters of a given treatment plan.

According to a further preferred embodiment, in response to receiving a user interaction with a slider, said radiotherapy planning system is configured to optimize an inner linear programming problem based on the adjusted weight. By responding to a user interaction in the described manner (i.e., with optimizing an inner linear programming problem based on the adjusted weight), the preferred embodiment moves towards the next best convex combination of Pareto solutions which satisfy the new/current sliders positions.

According to a further preferred embodiment, said graphical user interface is further configured to update and display respective dose maps and dose volume histograms. By updating and displaying respective dose maps and dose volume histograms, the preferred embodiment provides immediate feedback to planner on consequences of the user's selection.

As explained above, said radiotherapy planning system is configured to compare said solution to a clinical goal and wherein said radiotherapy planning system is further configured to generate a comparison signal indicative of whether or not the said solution satisfies said clinical goal. By comparing said solution to a clinical goal, the radiotherapy planning system according to the present invention may assist in deciding whether the present solution already provides a satisfactory treatment plan so that the iterative planning procedure may be stopped. Further, by generating a comparison signal indicative of whether or not the said solution satisfies said clinical goal, the radiotherapy planning system according to the present invention enables the user to decide upon being queried whether to continue or not. Alternatively and/or additionally, a user may set the preference to automatically stop the treatment planning procedure once a satisfactory solution (i.e., a solution satisfying one or more clinical goals) is found.

According to a further preferred embodiment, if said comparison signal indicates that said solution satisfies said clinical goal, said radiotherapy planning system is further configured to deliver the said solution to a radiation therapy system. If a current solution satisfies one or more clinical goals, the iterative treatment planning procedure may be stopped, because a satisfactory solution has been found. Radiation therapy may then commence right away or after a certain time period. In any case, it is preferable to transmit the determined solution to a radiation therapy system in order to have the treatment plan ready to be used.

According to a further preferred embodiment, said radiotherapy planning system is configured to employ a Pareto-front based refinement technique. By employing a Pareto-front based refinement technique, the radiotherapy planning system according to the preferred embodiment avoids an additional lengthy manual parameter tweaking to refine the auto-generated solution. Thereby, the radiotherapy planning system according to the preferred embodiment increases planner control on the auto-generated plan refinement process.

According to a further preferred embodiment, said radiotherapy planning system is configured to determine a set of treatment plans which sample a Pareto frontier. By determining a set of treatment plans which sample a Pareto frontier, fast and interactive browsing through various treatment options is possible.

According to a further preferred embodiment, said radiotherapy planning system is configured to determine a set of N+2 treatment plans, wherein N corresponds to the number of dose quality metrics, wherein said radiotherapy planning system is configured to determine N anchor treatment plans by optimizing each dose quality metric individually, and wherein said radiotherapy planning system is further configured to determine one additional balance treatment plan by using the same weight for each dose quality metric. By initially generating a set of plans via auto-planning using different combinations of the auto-planning settings' slider positions, a real-time interactive Pareto navigator can be deployed to increase planner control on the auto-generated plan refinement process in complex clinical scenarios.

According to a further preferred embodiment, said radiotherapy planning system is configured to build an approximated Pareto front by generating convex linear combinations of said one or more auto-planned treatment plans. By generating convex linear combinations of said one or more auto-planned treatment plans, the radiotherapy planning system according to the preferred embodiment achieves that the subsequent solution search (i.e., Pareto navigation) will be bounded to a local neighborhood of the auto-planned solutions.

According to a further preferred embodiment, said radiotherapy planning system is configured to normalize each of said one or more dose quality metrics.

According to a second aspect of the present invention, there is provided a radiotherapy planning method for determining a solution corresponding to a fluence profile, the radiotherapy planning method comprising the steps of generating one or more auto-planned treatment plans based on one or more dose quality metrics; assigning a predetermined plurality of weights to said one or more dose quality metrics; adjusting a selected weight from said plurality of weights; generating said solution corresponding to said fluence profile in response to said adjusted selected weight; comparing said solution to a clinical goal; and generating a comparison signal indicative of whether or not said solution satisfies said clinical goal.

According to a third aspect of the present invention, there is provided a computer readable storage medium encoded with one or more computer executable instructions, which, when executed by a processor of a computing system causes the processor to: generate one or more auto-planned radiotherapy treatment plans based on one or more dose quality metrics; assign a predetermined plurality of weights to said one or more dose quality metrics; adjust a selected weight from said plurality of weights; generate a solution corresponding to a fluence profile in response to said adjusted selected weight; compare said solution to a clinical goal; and generate a comparison signal indicative of whether or not said solution satisfies said clinical goal.

It shall be understood that the radiotherapy planning system of claim 1, the radiotherapy planning method of claim 12, and the computer readable storage medium of claim 13 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
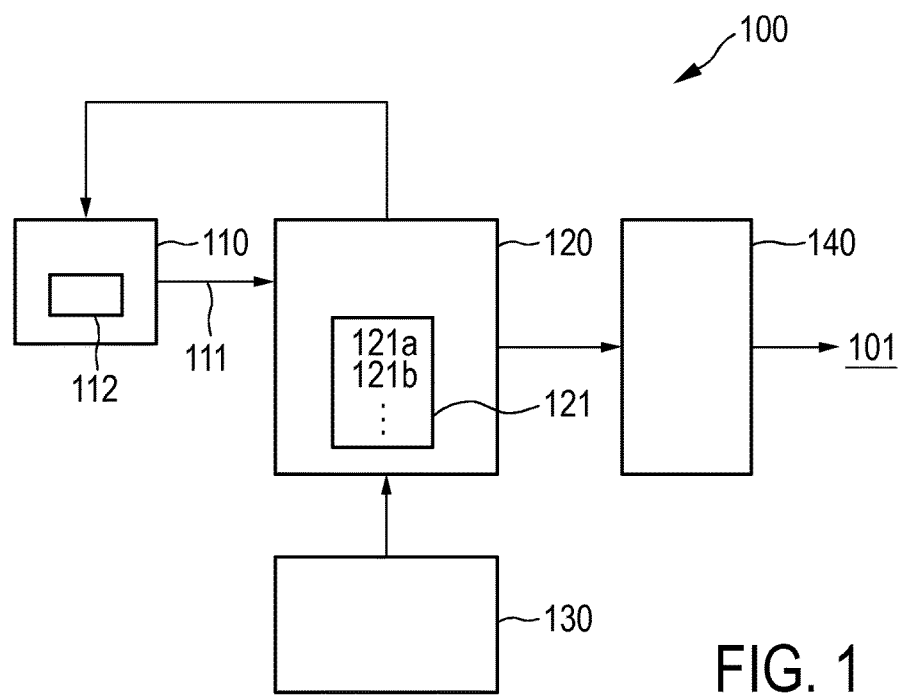
FIG. 1 shows schematically and exemplarily an embodiment of a radiotherapy planning system.

FIG. 1 shows schematically and exemplarily an embodiment of a radiotherapy planning system 100 for determining a solution 101 corresponding to a fluence profile. Radiotherapy planning system 100 comprises an auto-planned solution generation unit 110 for automatically generating one or more auto-planned treatment plans 111 based on one or more dose quality metrics 112; a weight assignment unit 120 configured to assign a predetermined plurality of weights 121 to said one or more dose quality metrics 112; a weight adjustment unit 130 configured to adjust a selected weight 121a from said plurality of weights 121; and a Pareto frontier navigation unit 140 configured to generate said solution 101 corresponding to said fluence profile in response to said adjusted selected weight 121a.

Figure 2:
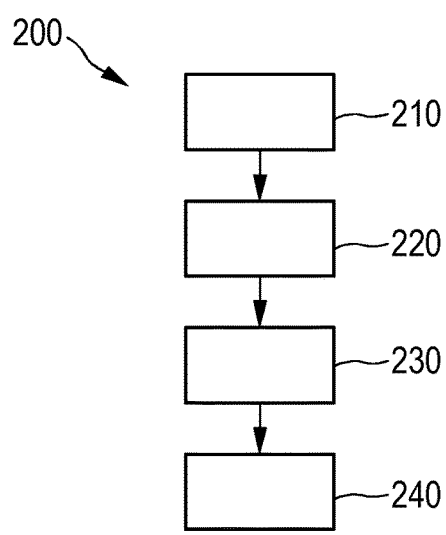
FIG. 2 shows schematically and exemplarily another embodiment of a radiotherapy planning method.

FIG. 2 shows schematically and exemplarily another embodiment of a radio-therapy planning method 200 for determining a solution 101 corresponding to a fluence profile, the radiotherapy planning method 200 comprising the steps of generating (step 210) one or more auto-planned treatment plans 111 based on one or more dose quality metrics 112; assigning (step 220) a predetermined plurality of weights 121 to said one or more dose quality metrics 112; adjusting (step 230) a selected weight 121a from said plurality of weights 121; and generating (step 240) said solution 101 corresponding to said fluence profile in response to said adjusted selected weight 121a.

Figure 3:
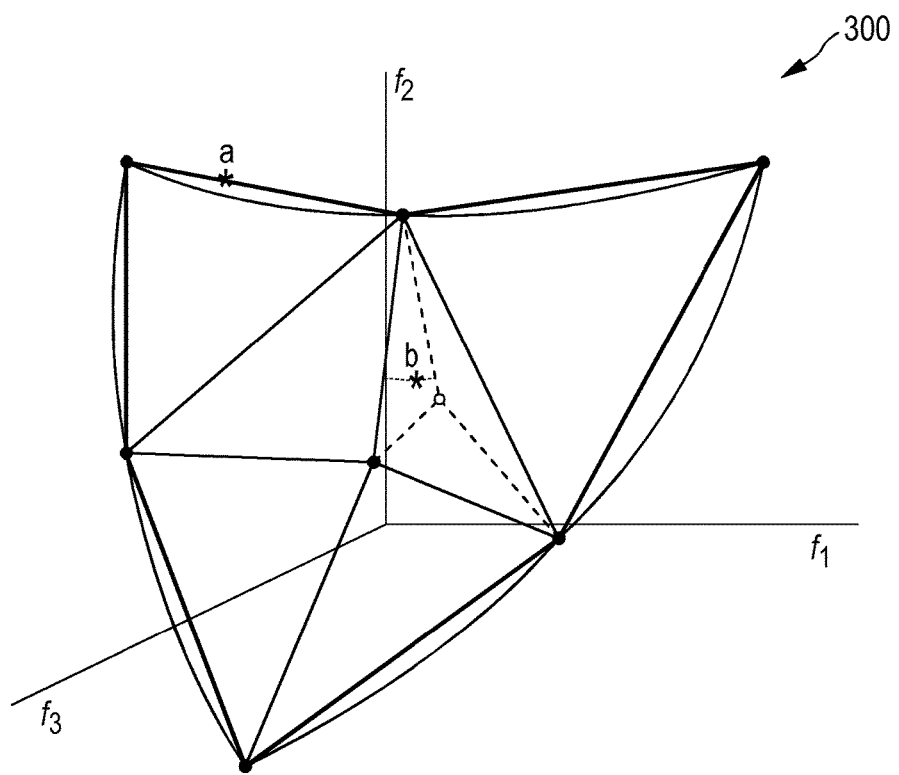
FIG. 3 shows schematically and exemplarily an illustration of a three dimensional Pareto surface.

FIG. 3 shows schematically and exemplarily an illustration 300 of a three dimensional Pareto surface as described, e.g., in the article "*Deliverable navigation for multicriteria step and shoot IMRT treatment planning*", Phys. Med. Biol. (2013), Vol. 58, pp. 87-103, by D. Craft and C. Richter. Auto-generated treatment plans are indicated by bold black dots. Convex combinations of those auto-generated treatment plans correspond to the triangles formed by respective three solution points. The mentioned convex combinations of auto-generated solutions approximate a three-dimensional Pareto surface. Further details are described in the above-mentioned article by Craft and Richter.

Auto-Planned Solution Generation

In a zero-th step, a potential solution (such as, e.g., a set of fluence beam profiles) may be determined, e.g., by using the Auto-planning Pinnacle$^3$ tool, as described in the article "*MO-D-BRB-07: Automated IMRT Plan Generation for Prostate Cancer*", Med. Phys. (2010), Vol. 37, pp. 3340-3340 by R. Kashani et al., which is incorporated herein by reference. If the auto-generated solution already satisfies all clinical wishes, then the plan can be readily delivered. If however due to different causes, the new dose distribution is not accurate enough, an additional lengthy manual parameter tweaking is needed to refine the auto-generated solution.

Figure 4:
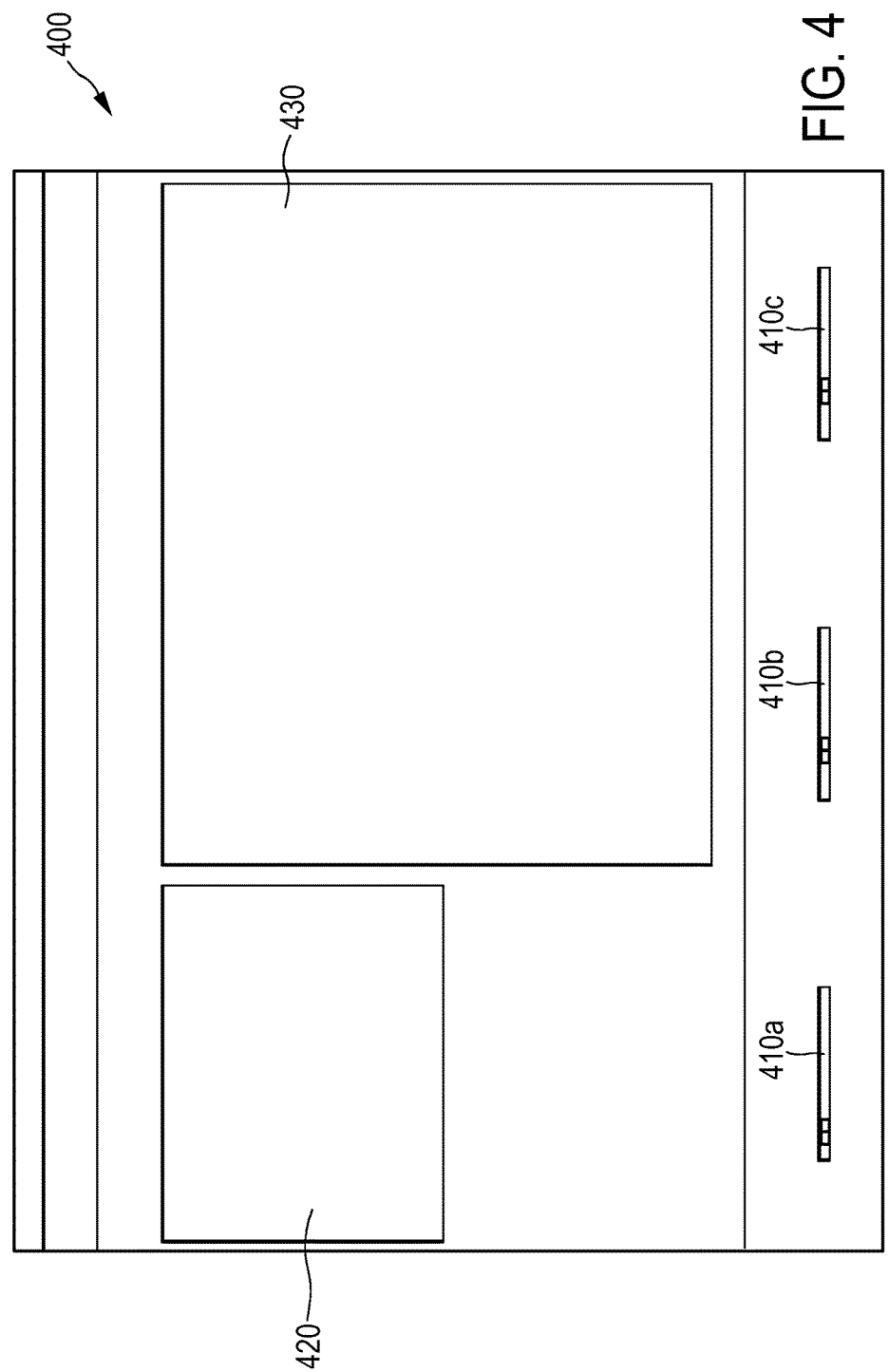
FIG. 4 shows schematically and exemplarily a screenshot of an auto-planning tool.

"Auto-planning" routines are available in the Philips Pinnacle$^3$ treatment planning system. FIG. 4 shows schematically and exemplarily a screenshot 400 of an auto-planning tool to be used, e.g., with the Philips Pinnacle$^3$ treatment planning system. Target optimization goals are shown in panel 420. OAR optimization goals are shown in panel 430. Said auto-planning routines rely on machine-readable instructions herein referred to as Pinnacle 'scripts'. Pinnacle scripts correspond to assemblies of internal commands. Preferably, scripts can be called at any time on new patient files. When invoked on a new patient, the auto-planning routine creates various target and normal tissue planning structures, sets the beams and dose prescription, and loads customized intensity modulated radiation therapy objectives to start the optimization. The target objectives are typically based on a given prescription dose, while organ at risk objectives are determined from a model that takes into account geometric properties of the target and organs at risk to predict mean doses based on prior cases. The auto-planning solutions could require more frequent intercession during optimization due to the model's occasional overemphasize of organs at risk sparing. In these cases, the planner is asked to tweak N "refinement" sliders (for instance, N=3) 410a, 410b, 410c related to different dose quality metrics as: "Target/organs at risk balance", "Dose falloff", "Conformality/Reduced-MU modulation", etc., as explained in the above-mentioned article "*MO-D-BRB-07: Automated IMRT Plan Generation for Prostate Cancer*", Med. Phys. (2010), Vol. 37, pp. 3340-3340 by R. Kashani et al. Subsequently, scripts are recalled with this new set of auto-planning parameters to determine a new auto-planned solution which better fits the planner requirements. This iterative manual refinement process can be very long and is not real-time interactive. In some complex clinical sites, it could take up to several hours to find the best solution, hampering the benefits of auto-planning on large efficiency gains and robust quality control of the clinical RTP process.

Localized Pareto Frontier Approximation

As explained above, at step 0, a first 'auto-generated' solution is produced, e.g., by using the Pinnacle 3 Auto-planning tool. Then, the planner may choose to accept and deliver this solution (i.e., beam fluence profiles) or to refine it.

If a refinement is desired, then the present invention can be used to make the refinement step easier and faster.

To this end, in a first step, a Pareto front approximation is determined by optimizing N+1 plans as described in more detail below. Since one wants to "refine" the first solution produced at step 0, a Pareto matrix Y will be populated with (N+1)+1=N+2 plans (i.e., N "anchor" plans, plus the "balance" plan, plus the initial auto-generated plan at step 0). Hereto, all dose quality metrics values for each solution $x_k$, with k=1, . . . , N+2, are normalized and used to populate a Pareto matrix Y=[f($x_1$)|f($x_2$)| . . . |f($x_{N+1}$), f($x_{N+2}$)]. Here, f is a vector-valued function, where each component is one of the N dose quality metrics (refinement sliders) discussed at step 0.

The normalized Y Pareto matrix is stored in memory and used to determine the convex hull piecewise linear approximation $Y^c$ of the Pareto front, $Y^c=Y*v$:

$$Y^c = \left\{ \sum_{k=1}^{N+2} v_k f(x_k) \middle| \sum_{k=1}^{N+2} v_k = 1, v \geq 0 \right\}.$$

Here v is the vector of convex combination weights for each navigated solution in $Y^c$. The initial $v_{ini}$ values will be the ones related to the plan optimized at step 0, i.e. the plan the planner is willing to further refine.

Since the matrix Y is normalized between [0,1] and since the coefficients $v_k$ may have values between 0 and 1, and since $$\sum_k v_k = 1,$$

the current sliders positions/values (which are also normalized in the interval [0,1]) can be used to find the best set of coefficients v* by means of linear programming. From these, one may recover and display the corresponding navigated solution as $$x^* = \sum_{k=1}^{N+2} v_k^* x_k$$

and the N sliders position f(x*)=Yv*. The slider's position f(x*) can be de-normalized back to the initial ranges before displaying it on the GUI.

In a first step, in case the optimal auto-generated solution determined at the zero-th step is not accurate enough, it is proposed to use a Pareto frontier navigator, as described in the article "*Deliverable navigation for multicriteria step and shoot IMRT treatment planning*", Phys. Med. Biol. (2013), Vol. 58, pp. 87-103, by D. Craft and C. Richter, which is incorporated herein by reference. By using a Pareto frontier navigator, the aim is to find the best final plan within a local neighborhood of a limited set of auto-planned solutions $x_k$, where a "solution" corresponds to a specific fluence beam profile. The first step in Pareto navigation thus corresponds to determining a set of plans, which accurately sample the Pareto frontier. This set of plans shall be referred to as Pareto database plans. In this specific case, it is proposed to build an approximated Pareto frontier using a limited set of sub-optimal auto-planned solutions $x_k$ and all their convex linear combinations, i.e., all their linear combinations, where the coefficients are non-negative and sum to 1. In this way, the subsequent solution search (i.e., Pareto navigation) will be bounded to a local neighborhood of the auto-planned solutions $x_k$.

Consider $$v^* = \mathrm{argmin}\{z \in \mathfrak{R} \mid (Yv)_i - y_i^R + s_i = z, i \in \kappa\setminus\{j\}, (Yv)_j = \tau, \sum_{i=1}^{N+2} v_i = 1, s \geq 0\}.$$

When solving this linear problem, one looks for a new set of coefficients v*

$$\left(\text{i.e., a new solution } x^* = \sum_{k=1}^{N+2} v_k^* x_k\right)$$

where all i-th dose quality metrics values are kept very close to one of the previous solution $(Yv)_i - y_i^R + s_i = z$, except the j-th dose quality metric value (the one related to the slider which was modified by the user in the GUI). In this way, it is ensured that the "navigation" throughout the solution space is smooth and the new position is as close (local) as possible to the previous position/solution.

In complex clinical scenarios, a real-time interactive Pareto navigator as described in the above-mentioned article "*Deliverable navigation for multicriteria step and shoot IMRT treatment planning*", Phys. Med. Biol. (2013), Vol. 58, pp. 87-103, by D. Craft and C. Richter, can be deployed to increase planner control on the auto-generated plan refinement process. Initially, a set of plans are generated via auto-planning using different combinations of the auto-planning settings' slider positions. For example, one idea could be to determine N plans, which shall be referred to as "anchor plans", by optimizing each k-th quality metric. In other words, one plan for each quality metric is optimized individually. This means that the slider position of one metric is set to its maximum value, while all other sliders are set to the minimum. Then, the sliders' positions are used, e.g., by the Pinnacle 3 Auto-planning tool, to obtain one auto-generated solution. This solution is collected in the Pareto matrix Y.

One additional "balance" plan is optimized using the same weight for each quality metric. The name "balance plan" has been chosen to reflect that all weights are the same, i.e., all tuning parameters are equally important. Once the initial set of refined auto-planned solutions is available, the initial set of refined auto-planned solutions can be used to approximate and navigate the Pareto solution space. Preferably, all dose quality metrics values for each solution $x_k$, with k=1, . . . , N+2, are normalized and used to populate a Pareto matrix $Y=\lfloor f(x_1)|f(x_2)| \ldots |f(x_{N+2})\rfloor$. Here, f is a vector-valued function, where each component is one of the N dose quality metrics (refinement sliders) discussed at the zero-th step described above. If one of the N+2 anchor plans is already satisfying all clinical goals, the solution is kept and delivered to the patient. If this is not the case, an interactive real-time Pareto navigator is applied to move to a better solution point.

Figure 5:
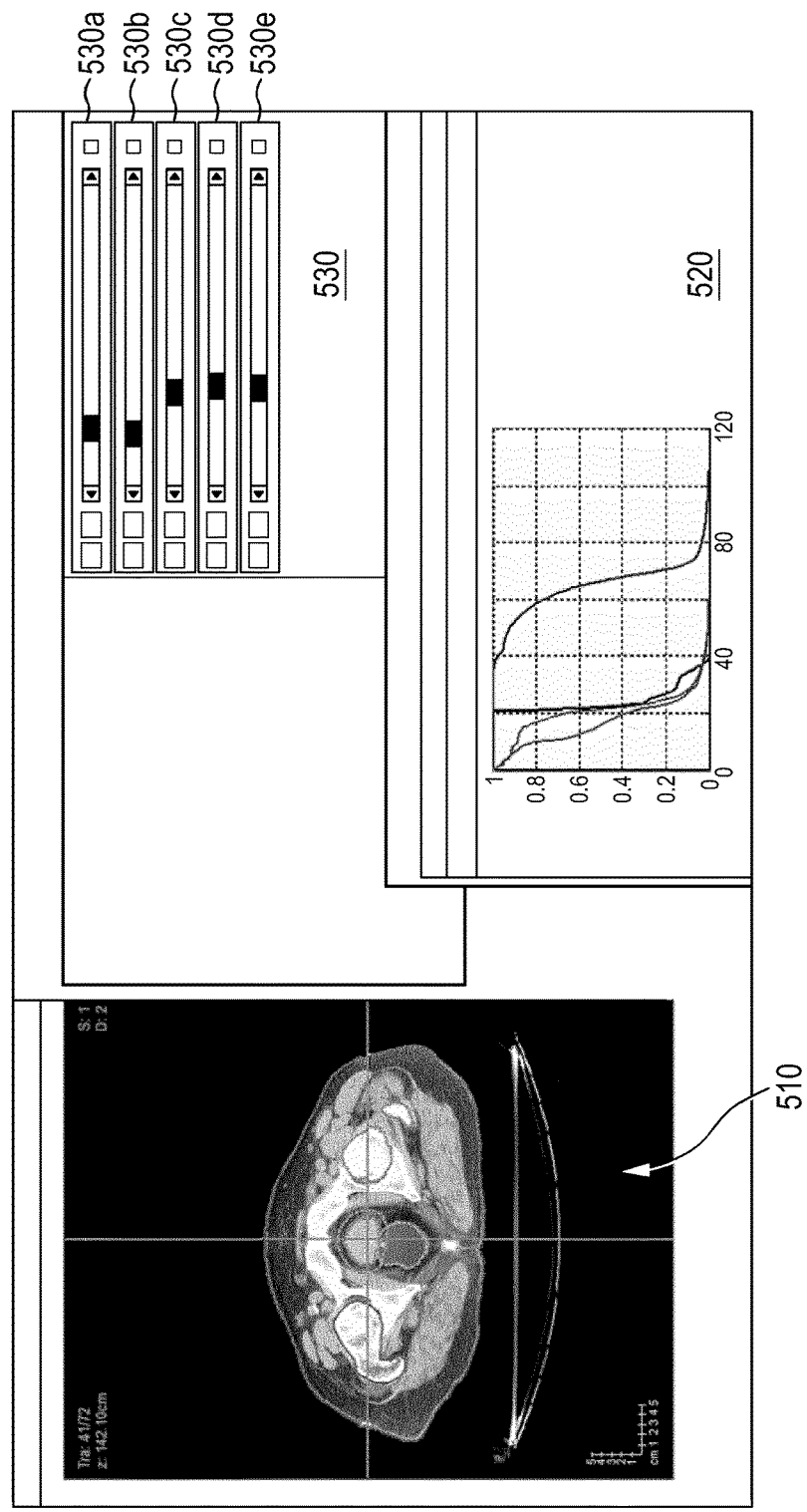
FIG. 5 shows schematically and exemplarily a screenshot of a Pareto navigator tool.

FIG. 5 shows schematically and exemplarily a screenshot of a Pareto navigator tool. Current plots of dose distribution 510 and the corresponding dose-volume-histograms 520 are displayed. In addition, Pareto navigation sliders 530a, . . . , 530e (collectively referred to as Pareto navigation slider 530) are depicted. Here, every time one slider 530 is moved, dose distribution 510 and the corresponding dose-volume-histograms 520 are updated in real-time with an update time of approximately one second or less.

Pareto Frontier Navigator

Figure 6:
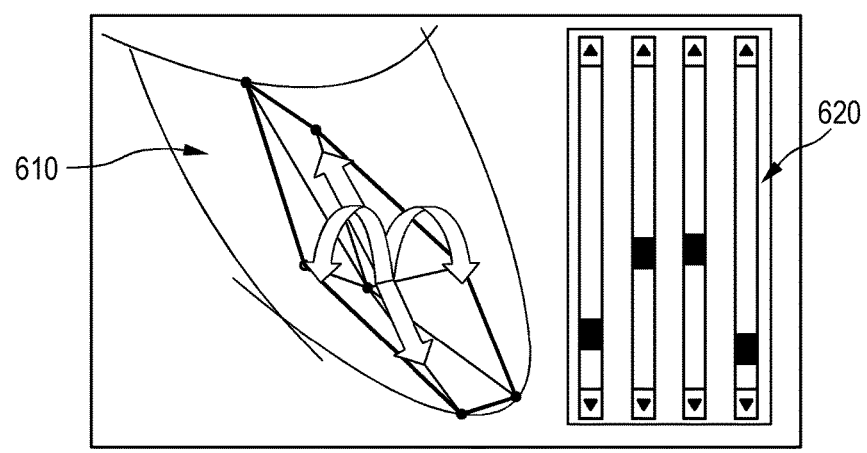
FIG. 6 shows schematically and exemplarily an illustration of a Pareto navigator tool slider movement.

Once the approximated Pareto frontier (i.e., a Pareto matrix Y) is given, a second step corresponds to providing a tool that allows the planner to navigate within the Pareto optimal space in order to find the best trade-off between all target and organ at risk's dose objectives. Herein, it is proposed to provide the planner with a simple and interactive graphical user interface, where for at least one (preferably for each) of the tuning parameters a slider is provided to increase/decrease its importance, as illustrated in FIG. 6. FIG. 6 shows schematically and exemplarily an illustration of a Pareto navigator tool slider movement. For instance, in a preferred embodiment, every time one of the sliders is moved to increase or decrease the corresponding dose quality measure, a linear programming problem is solved to move from the reference point towards a new point on the approximated local Pareto front.

The term "slider" is generally used in computing to refer to a Graphical User Interface element used to set a value by moving an indicator, e.g., in a horizontal or vertical fashion. By moving the slider of a respective one of the tuning parameters, the tuning parameter's weight in a linear approximation problem is increased or decreased. Preferably, every time a slider is moved, this action invokes the optimization of an inner linear programming problem, which aims to "move" towards the next best convex combination of Pareto solutions which satisfy the new sliders positions. Accordingly, the user is given a real-time feedback about the quality of the new position at current sliders positions. The present invention however also covers solutions using triggers to update less frequently, although linear programming optimization is very fast so that always updating is not an issue.

During Pareto frontier navigation the corresponding dose map and dose volume histograms (DVHs) are preferably continuously updated and plotted (where the update time is, e.g., less than 1 s).

The proposed navigator will move within a convex hull piecewise linear approximation $Y^c$ of the Pareto front, as described in the article "*Pareto navigation—algorithmic foundation of interactive multi-criteria IMRT planning*", Phys. Med. Biol. (2008), Vol. 53, pp. 985-998, by M. Monz et al., which is incorporated herein by reference:

$$Y^c = \left\{ \sum_{k=1}^{N+2} v_k f(x_k) \,\middle|\, \sum_{k=1}^{N+2} v_k 1, v \geq 0 \right\}.$$

Here v is the vector of convex combination weights for each navigated solution in $Y^c$. In mathematics, the convex hull or convex envelope of a set X of points in Euclidean space is the smallest convex set that contains X. For instance, when X is a bounded subset of the plane, the convex hull may be visualized as the shape formed by a rubber band stretched around X, see the textbook "*Computational Geometry: Algorithms and Applications*", Springer, pp. 2-8, 2000, by de Berg, M.; van Kreveld, M.; Overmars, Mark; Schwarzkopf, O. Formally, the convex hull may be defined as the intersection of all convex sets containing X or as the set of all convex combinations of points in X. With the latter definition, convex hulls may be extended from Euclidean spaces to arbitrary real vector spaces; they may also be generalized further, to oriented matroids, see the textbook "*Axioms and hulls*", Lecture Notes in Computer Science no. 606, Heidelberg: Springer-Verlag, p. ix+109, doi:10.1007/3-540-55611-7, ISBN 3-540-55611-7, MR 1226891, 1992, by Knuth, Donald E.

Herein, it is proposed to offer the planner a simple and interactive graphic user interface, where for each quality metric to tune a slider is provided to change its value (as illustrated in FIG. 5). Preferably every time a slider is moved, this action invokes the minimization of an inner linear programming problem, which aims to find the best set of weights v* in order to "move" towards the next best convex combination x* of the auto-generated solutions $x_k$ which satisfy the current sliders positions:

$$v^* = \mathrm{argmin}\{z \in \Re \mid (Yv)_i - y_i^R + s_i =$$
$$z, i \in \kappa\backslash\{j\}, (Yv)_j = \tau, \sum_{i=1}^{N+2} v_i = 1, s \geq 0\},$$

where arg min stands for the argument of the minimum, that is to say, v* corresponds to the set of points $z \in \Re$ of the given argument for which the given function $$(Yv)_i - y_i^R + s_i = z, i \in \kappa\backslash\{j\}, (Yv)_j = \tau, \sum_{i=1}^{N+2} v_i = 1, s \geq 0$$

attains its minimum value. Here, j is the index of the moved slider, τ is the slider selected value, κ:={1, . . . , N} is the set of sliders indices, and s are slack variables, i.e. variables that are added to an inequality constraint to transform it to an equality, see the book "*Convex Optimization*", Cambridge University Press. ISBN 978-0-521-83378-3, 2004, by Boyd, Stephen P.; Vandenberghe, Lieven, which is incorporated herein by reference. The reference point $y^R$ represents a vector with N entries corresponding to the sliders' positions before the j-th slider was moved. Hence, the τ value is enforced for the j-th metric and one looks for the best distance to the previous sliders positions in the remaining quality criteria. During Pareto frontier navigation the corresponding navigated solution (i.e., fluence map) $x_k$ can be computed using the very same optimized weights v*:

$$x^* = \sum_{k=1}^{N+2} v_k^* x_k.$$

Corresponding dose map and dose volume histograms can also be computed and displayed preferably continuously (with a preferred update time of less than one second), as described in the above-mentioned article "*Pareto navigation—algorithmic foundation of interactive multi-criteria IMRT planning*", Phys. Med. Biol. (2008), Vol. 53, pp. 985-998, by M. Monz et al. An example of a navigator graphical user interface is shown in FIG. 5.

Subsequent Processing

In an additional step, if the final navigated plan x* satisfies all clinical goals, the corresponding solution (i.e., fluence beam profiles) can be readily delivered. If on the other hand the Pareto approximation is not accurate enough, the optimal set of tuning parameters (i.e., navigated parameters) may be used as warm start to generate a final auto-generated plan. In other words, the Pareto navigated solution x* (i.e., the beam profile) could be further processed by a traditional IMRT fluence map optimization tool (available in all radiation therapy planning tools, such as, e.g., the Pinnacle 3).

The proposed invention can be applied to all clinical cases where a conventional treatment planning system employing only auto-planning fails to produce IMRT plans which meet the required quality. Large efficiency gains, real-time interaction and robust quality control on the clinical IMRT planning process would appear possible by extending treatment planning systems with such a Pareto navigator tool.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like determining a convex hull piecewise linear approximation of a Pareto front, determining a set of treatment plans which sample a Pareto frontier, determining a set of N+1 treatment plans, determining N anchor treatment plans, determining one additional balance treatment plan, et cetera performed by one or several units or devices can be performed by any other number of units or devices. For example, the determination of a convex hull piecewise linear approximation of a Pareto front can be performed by a single unit or by any other number of different units. The control of the radiotherapy planning system in accordance with the above described radio-therapy planning method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The present invention relates to a radiotherapy planning system for determining a solution corresponding to a fluence profile. The invention proposes to use a Pareto frontier navigator to select the best plan from a set of various auto-planned solutions. An interactive graphical user interface is provided to the planner to navigate among convex combinations of auto-planned solutions. This proposed Pareto plan navigation can be considered as a further optional refinement process, which can be applied to find the best plan in those cases where auto-generated solutions are not fully satisfying the planner's requirements. The navigation tool moves locally through a set of auto-generated plans and can potentially simplify the planner's decision making process and reduce the whole planning time on complex clinical cases from several hours to minutes.

The invention claimed is:

1. A radiotherapy planning system for determining a solution corresponding to a fluence profile, the radiotherapy planning system comprising:
    an auto-planned solution generation unit for automatically generating one or more auto-planned treatment plans based on one or more dose quality metrics;
    a weight assignment unit configured to assign a predetermined plurality of weights to said one or more dose quality metrics;
    a weight adjustment unit configured to adjust a selected weight from said plurality of weights; and
    a Pareto frontier navigation unit configured to generate said solution corresponding to said fluence profile in response to said adjusted selected weight;
    wherein said radiotherapy planning system is configured to compare said solution to a clinical goal and wherein said radiotherapy planning system is further configured to generate a comparison signal indicative of whether or not said solution satisfies said clinical goal and to provide said solution as a warm start to generate a final auto-generated plan, if said comparison signal indicates that said solution does not satisfy said clinical goal.

2. The radiotherapy planning system of claim 1, wherein said Pareto frontier navigation unit is configured to determine a convex hull piecewise linear approximation of a Pareto front.

3. The radiotherapy planning system of claim 1, wherein said weight adjustment unit comprises a graphical user interface, where, for each respective weight from said plurality of weights, a slider is provided to adjust said respective weight.

4. The radiotherapy planning system of claim 3, wherein, in response to receiving a user interaction with a slider, said radiotherapy planning system is configured to optimize an inner linear programming problem based on the adjusted weight.

5. The radiotherapy planning system of claim 3, wherein said graphical user interface is further configured to update and display respective dose maps and dose volume histograms.

6. The radiotherapy planning system of claim 1, wherein, if said comparison signal indicates that said solution satisfies said clinical goal, said radiotherapy planning system is further configured to deliver the said solution to a radiation therapy system.

7. The radiotherapy planning system of claim 1, wherein said radiotherapy planning system is configured to employ a Pareto-front based refinement technique.

8. The radiotherapy planning system of claim 1, wherein said radiotherapy planning system is configured to determine a set of treatment plans which sample a Pareto frontier.

9. The radiotherapy planning system of claim 1, wherein said radiotherapy planning system is configured to determine a set of N+1 treatment plans, wherein N corresponds to the number of dose quality metrics, wherein said radiotherapy planning system is configured to determine N anchor treatment plans by optimizing each dose quality metric individually, and wherein said radiotherapy planning system is further configured to determine one additional balance treatment plan by using the same weight for each dose quality metric.

10. The radiotherapy planning system of claim 1, wherein said radiotherapy planning system is configured to build an approximated Pareto front by generating convex linear combinations of said one or more auto-planned treatment plans.

11. The radiotherapy planning system of claim 1, wherein said radiotherapy planning system is configured to normalize each of said one or more dose quality metrics.

12. A radiotherapy planning method for determining a solution corresponding to a fluence profile, the radiotherapy planning method comprising the steps of
    generating one or more auto-planned treatment plans based on one or more dose quality metrics;
    assigning a predetermined plurality of weights to said one or more dose quality metrics;
    adjusting a selected weight from said plurality of weights;
    generating said solution corresponding to said fluence profile in response to said adjusted selected weight by using a Pareto frontier navigation unit;
    comparing said solution to a clinical goal; and
    generating a comparison signal indicative of whether or not said solution satisfies said clinical goal, wherein, if said comparison signal indicates that said solution does not satisfy said clinical goal, said solution is provided as a warm start to generate a final auto-generated plan.

13. A computer readable storage medium encoded with one or more computer executable instructions, which, when executed by a processor of a computing system causes the processor to carry out the steps of the radiotherapy planning method defined by claim 12.

* * * * *